United States Patent
Dahl et al.

(10) Patent No.: US 10,457,718 B2
(45) Date of Patent: Oct. 29, 2019

(54) COMPOUNDS FOR THE TREATMENT OF CANCER

(71) Applicant: Rheinisch-Westfaelische Technische Hochschule Aachen, Aachen (DE)

(72) Inventors: Edgar Dahl, Kelmis (BE); Michael Rose, Herzogenrath (DE); Sebastian Huth, Aachen (DE)

(73) Assignee: Rheinisch-Westfaelische Technische Hochschule Aachen, Aachen (DE)

( * ) Notice: Subject to any disclaimer, the term of this patent is extended or adjusted under 35 U.S.C. 154(b) by 0 days.

(21) Appl. No.: 15/541,660

(22) PCT Filed: Jan. 6, 2016

(86) PCT No.: PCT/EP2016/050100
§ 371 (c)(1),
(2) Date: Jul. 5, 2017

(87) PCT Pub. No.: WO2016/110496
PCT Pub. Date: Jul. 14, 2016

(65) Prior Publication Data
US 2017/0362303 A1  Dec. 21, 2017

(30) Foreign Application Priority Data

Jan. 6, 2015 (EP) .................... 15150219

(51) Int. Cl.
*A61K 38/57* (2006.01)
*C07K 14/81* (2006.01)
*A61K 38/00* (2006.01)

(52) U.S. Cl.
CPC ............ *C07K 14/811* (2013.01); *A61K 38/00* (2013.01)

(58) Field of Classification Search
None
See application file for complete search history.

(56) References Cited

U.S. PATENT DOCUMENTS

2002/0132981 A1  9/2002  Baker et al.

FOREIGN PATENT DOCUMENTS

| WO | 2000/55375 | 9/2000 | |
|----|----|----|----|
| WO | WO-0154477 A2 * | 8/2001 | ............. C07K 14/47 |
| WO | 2003/100016 | 12/2003 | |
| WO | 2013135836 A1 | 9/2013 | |

OTHER PUBLICATIONS

PCT/EP2016/050100 International Search Report dated Mar. 17, 2016.
Kloten et al., "Epigenetic Inactivation of the Novel Candidate Tumor Suppressor Gene ITIH5 in Colon Cancer Predicts Unfavorable Overall Survival in the CpG Island Methylator Phenotype." Epigenetics, Sep. 2014, 9(9):1290-1301, Landes Bioscience.
Rose et al., "Epigenetic Inactivation of ITIH5 Promotes Bladder Cancer Progression and Predicts Early Relapse of pT1 High-Grade Urothelial Tumours." Carcinogenesis, 2014, 35(3):727-736.
Rose, "Identification and validation of new DNA methylation biomarkers for the early detection of bladder tumors and characterization of the putative tumor suppressor gene ITIH5 for bladder and breast carcinoma," May 13, 2013, pp. 3pp.I-XIV, [Retrieved from the InternetJun. 3, 2015]: URL:http://publications.rwth-aachen.de/record/229798/files/4573.pdf.

* cited by examiner

*Primary Examiner* — Julie Ha
*Assistant Examiner* — Kristina M Hellman
(74) *Attorney, Agent, or Firm* — Wagenknecht IP Law Group, PC

(57) ABSTRACT

The technology provided herein relates to novel isolated polypeptides and peptides having a growth inhibitory effect on human cancer cells. Nucleic acid molecules encoding said polypeptides/peptides, vectors, host cells containing the nucleic acids and methods for preparation and producing said polypeptides/peptides. Compositions and methods for using such polypeptides/peptides for the prevention and treatment of cancer are also encompassed by the present disclosure.

2 Claims, 14 Drawing Sheets

Specification includes a Sequence Listing.

FIGURE 2
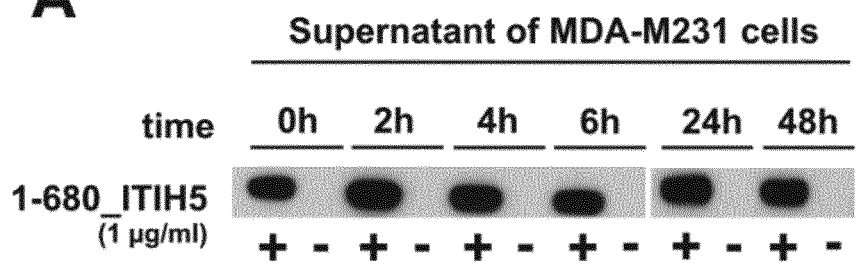
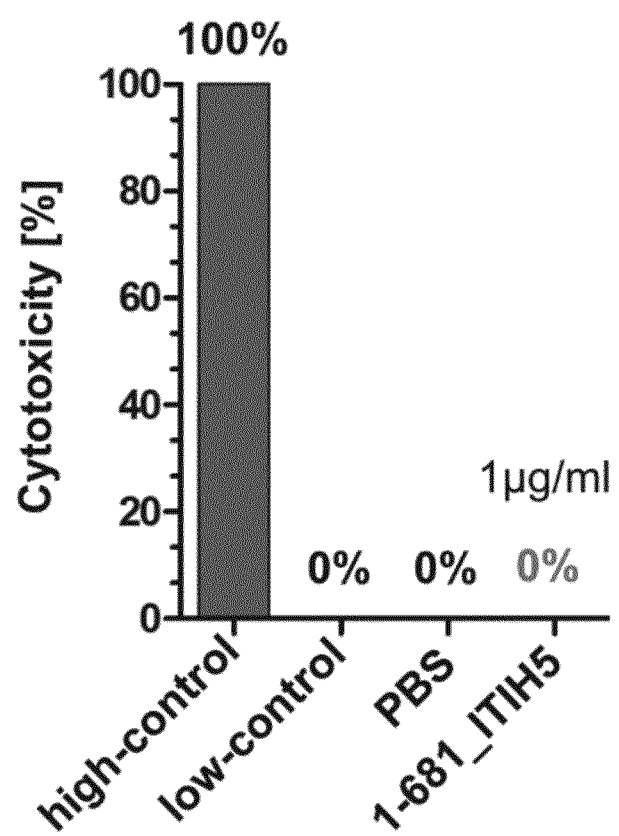

FIGURE 7

Amino acid sequence of the isolated polypeptide 1-681_ ITIH5 (SEQ ID NO: 1)

```
MLLLLGLCLG LSLCVGSQEE AQSWGHSSEQ DGLRVPRQVR LLQRLKTKPL MTEFSVKSTI
ISRYAFTTVS CRMLNRASED QDIEFQMQIP AAAFITNFTM LIGDKVYQGE ITEREKKSGD
RVKEKRNKTT EENGEKGTEI FRASAVIPSK DKAAFFLSYE ELLQRRLGKY EHSISVRPQQ
LSGRLSVDVN ILESAGIASL EVLPLHNSRQ RGSGRGEDDS GPPPSTVINQ NETFANIIFK
PTVVQQARIA QNGILGDFII RYDVNREQSI GDIQVLNGYF VHYFAPKDLP PLPKNVVFVL
DSSASMVGTK LRQTKDALFT ILHDLRPQDR FSIIGFSNRI KVWKDHLISV TPDSIRDGKV
YIHHMSPTGG TDINGALQRA IRLLNKYVAH SGIGDRSVSL IVFLTDGKPT VGETHTLKIL
NNTREAARGQ VCIFTIGIGN DVDFRLLEKL SLENCGLTRR VHEEEDAGSQ LIGFYDEIRT
PLLSDIRIDY PPSSVVQATK TLFPNYFNGS EIIIAGKLVD RKLDHLHVEV TASNSKKFII
LKTDVPVRPQ KAGKDVTGSP RPGGDGEGDP NHIERLWSYL TTKELLSSWL QSDDEPEKER
LRQRAQALAV SYRFLTPFTS MKLRGPVPRM DGLEEAHGMS AAMGPEPVVQ SVRGAGTQPG
PLLKKPYQPR IKISKTSVDG D
```

FIGURE 8

Amino acid sequence of the "VIT" domain of the inter-alpha-trypsin inhibitor heavy chain (ITIH) proteins (SEQ ID NO: 2)

```
MLLLLGLCLG  LSLCVGSQEE  AQSWGHSSEQ  DGLRVPRQVR  LLQRLKTKPL  MTEFSVKSTI
ISRYAFTTVS  CRMLNRASED  QDIEFQMQIP  AAAFITNFTM  LIGDKVYQGE  ITEREKKSGD
RVKEKRNKTT  EENGEKGTEI  FRASAVIPSK  DKAAFFLSYE  E
```

FIGURE 9

Amino acid sequence of the "vWA" domain of the inter-alpha-trypsin inhibitor heavy chain (ITIH) proteins (SEQ ID NO: 3)

```
GYF VHYFAPKDLP PLPKNVVFVL DSSASMVGTK LRQTKDALFT ILHDLRPQDR FSIIGFSNRI
KVWKDHLISV TPDSIRDGKV YIHHMSPTGG TDINGALQRA IRLLNKYVAH SGIGDRSVSL
IVFLTDGKPT VGETHTLKIL NNTREAARGQ VCIFTIGIGN DVDFRLLEKL SLENCGLTRR
VHEEEDAGSQ LIGFYDEIRT PLLSDIRIDY
```

FIGURE 10

Amino acid sequences of isolated peptides A) #26 (SEQ ID NO: 8) and B) #32 (SEQ ID NO: 9) derived from the ITIH5 VIT-domain (SEQ ID NO: 2)

A) #26 (SEQ ID NO: 8)

SVKSTIISRYAFTTVSCRML

B) #32 (SEQ ID NO: 9)

MLNRASEDQDIEFQMQIPAA

FIGURE 11

Amino acid sequences of isolated peptides A) #98 (SEQ ID NO: 4), B) #102 (SEQ ID NO: 5), C) #108 (SEQ ID NO: 6) and D) #111 (SEQ ID NO: 7) derived from the ITIH5 vWA domain (SEQ ID NO: 3)

A)  #98 (SEQ ID NO: 4)

GDIQVLNGYFVHYFAPKDLP

B)  #102 (SEQ ID NO: 5),

YFAPKDLPPLPKNVVFVLDS

C)  #108 (SEQ ID NO: 6)

DSSASMVGTKLRQTKDALFT

D)  #111 (SEQ ID NO: 7)

KLRQTKDALFTILHDLRPQD

COMPOUNDS FOR THE TREATMENT OF CANCER

CROSS REFERENCE TO RELATED APPLICATIONS

This is a US national phase application under 35 USC § 371 of international patent application no. PCT/EP2016/050100, filed Jan. 6, 2016, which itself claims priority to European application no. EP 15150219.2, filed Jan. 6, 2015. Each of the applications referred to in this paragraph are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing under the file name "PCTEP2016050100_SEQID" created on 3 Jul. 2017, filed on 5 Jul. 2017 and having a size of 12 Kilobytes. The sequence listing contained in this ASCII formatted document forms part of the specification and is herein incorporated by reference in its entirety.

FIELD OF THE INVENTION

The present disclosure relates to novel isolated polypeptides and peptides having a growth inhibitory effect on human cancer cells and, wherein said compounds are suitable for the use in treating cancer like breast cancer.

BACKGROUND

Cancer is one of the most prominent causes of human death. For example, breast cancer is one of the most common causes of cancer in women. The likelihood of developing invasive breast cancer during a woman's lifetime is approximately 1 in 7. In this aspect it is expected that the global market for breast cancer therapy and diagnosis is about 12 to 15 Billion US Dollar by 2015. There is an intense search for new compounds useful for the treatment and diagnosis of cancer, e.g. solid tumors, in particular breast cancer.

Anti-cancer drug discovery is now driven by the numerous cancer-specific molecular alterations identified in tumor cells over the past decade. To exploit these alterations, it is necessary to understand how they define a molecular context that allows increased sensitivity to particular compounds. Traditional genetic approaches together with the new wealth of genomic information in both human and model organisms open up strategies by which drugs can be profiled for their ability to selectively kill cells in a molecular context matching those found in tumors. Similarly, it may be possible to identify and validate new targets for drugs that would selectively kill tumor cells with a particular molecular context.

The recent remarkable progress in identifying cancer-specific molecular alterations in human tumors has unfortunately not been paralleled in the field of anti-cancer drug discovery. The shortage of effective anti-cancer drugs is due in part to the fundamental difficulties associated with the development of any safe and effective drug. For example, it remains a formidable task to design small molecules that alter the function of macromolecules with both sensitivity and specificity (for example, an enzyme with a small active site). It is even more difficult to inhibit protein-protein interactions mediated over a large surface, or to restore function to a defective protein (such as an inactive tumor suppressor gene). Even when successful, massive efforts are required—often measured in years to decades—from dozens of chemists, biochemists and toxicologists.

Considerable commercial and academic resources are directed to identification of candidate therapeutic agents for the treatment of various types of cancer. For example in case of breast cancer, herceptin was developed representing a humanised antibody approved for the treatment of HER2-positive metastatic breast cancer. Other newly designed therapeutic agents include humanised anti-CD20-antibodies, like Rituximab. A further example, Tykerb is a dual kinase inhibitor which inhibits both ErbB-2 and EGFR kinases and may be more effective than e.g. the compound herceptin.

Unfortunately, the vast majority of genes that show cancer-specific alterations in tumors do not present pharmaceutically tractable targets for the creation of small molecule therapeutics.

The most common molecular targets, which have proven useful in the identification of small molecule drugs, are enzymes, receptor-ligand pairs, and occasionally specific protein-protein interactions. Selective inhibitors of these types of molecular processes can readily be found that block the biochemical reactions carried out by these molecules (Gibbs, J. B. and Oliff, A., in Cell (1994) 79: 193-8). However, many of the genetic abnormalities found in human cancers represent loss of function mutations that eliminate or severely reduce the biochemical activities governed by these proteins. Since these molecules have already lost their normal biochemical activities, blockade of their physiological functions by drug inhibitors offers no therapeutic benefit. Thus, the list of potential cancer drug targets is much smaller than the long list of genes that are altered in human tumors.

Typically, the various types of cancers, for example breast cancer, are multifactorial diseases with no standardized medication available for patients. In spite of major advance in early detection and subsequent therapy, diagnosis and treatment as well as stratification of treatment regimen remains a major clinical and social problem.

Thus, the object of the present disclosure is to provide novel therapeutic agents for the use in prophylaxis or treatment of cancers, in particular for the treatment of breast cancer.

SUMMARY OF THE INVENTION

The present disclosure relates to novel biological compounds as therapeutic agents for the use in the prophylaxis or treatment of cancer.

In a first aspect, the present disclosure relates to isolated polypeptides having a growth inhibitory effect on human cancer cells, wherein said polypeptide is a fragment of the naturally occurring ITIH5-protein, and wherein said fragment consists of SEQ ID NO. 2, or a variant thereof, wherein said variant is at least 85% identical to the amino acid sequence of SEQ ID NO. 2.

These polypeptides may comprise few additional amino acids to the amino acid sequence of SEQ ID NO. 2, wherein the polypeptides have a length of about less than 200 amino acids, in particular of about less than 190 amino acids, in particular of about less than 180 amino acids, in particular of about less than 170 amino acids, in particular of about less than 165 amino acids.

Furthermore, embodiments of the present disclosure pertains to peptides having an amino acid sequence between 10 to 50 amino acids in length, in particular between 15 and 30 amino acids in length, in particular between 20 and 25 amino acids in length, wherein the peptide comprises an amino acid sequence derived from SEQ ID NO. 2. In particular, the peptides according to the present disclosure have an amino acid sequence of SEQ ID NO. 8 or SEQ ID NO. 9, or a variant thereof, wherein said variant is at least 85% identical to the amino acid sequence of SEQ ID NO. 8 or SEQ ID NO. 9.

Further embodiments of the disclosure relate to isolated polypeptides having a growth inhibitory effect on human cancer cells, wherein said polypeptide is a fragment of the naturally occurring ITIH5-protein, and wherein said fragment comprises SEQ ID NO. 2 and/or SEQ ID NO. 3, or variants thereof.

In particular, embodiments of the disclosure relate to isolated polypeptides having a growth inhibitory effect on human cancer cells, wherein said polypeptide is a fragment of a naturally occurring ITIH5-protein, and wherein said fragment comprises an amino acid sequence derived from SEQ ID NO. 1.

In a further aspect, embodiments of the disclosure relate to isolated polypeptides having a growth inhibitory effect on human cancer cells, wherein said polypeptide is a fragment of a naturally occurring ITIH5-protein, and wherein said fragment comprises the amino acid sequence of SEQ ID NO. 2, or a variant thereof, wherein said variant is at least 85% identical to the amino acid sequence of SEQ ID NO. 2.

In a further aspect, embodiments of the disclosure relate to isolated polypeptides having a growth inhibitory effect on human cancer cells, wherein said polypeptide is a fragment of a naturally occurring ITIH5-protein, and wherein said fragment comprises the amino acid sequence of SEQ ID NO. 3, or a variant thereof, wherein said variant is at least 85% identical to the amino acid sequence of SEQ ID NO. 3.

In a further aspect, embodiments of the disclosure relate to isolated peptides having a growth inhibitory effect on human cancer cells, wherein said peptides comprise an amino acid sequence derived from SEQ ID NO. 2 or SEQ ID NO. 3.

Furthermore, embodiments of this disclosure relate to isolated polypeptides having a growth inhibitory effect on human cancer cells, wherein said polypeptide is a fragment of the naturally occurring ITIH5 protein, wherein said polypeptide comprises the amino acid sequence of the VIT-domain (SEQ ID NO. 2) of ITIH5 protein, or a variant thereof, wherein said variant is at least 85% identical to the amino acid sequence of SEQ ID NO. 2, or said polypeptide comprises an amino acid sequence derived from the VIT-domain (SEQ ID NO. 2) or from said variant.

Furthermore, embodiments of this disclosure relate to isolated polypeptides having a growth inhibitory effect on human cancer cells, wherein said polypeptide is a fragment of the naturally occurring ITIH5 protein, wherein said polypeptide comprises the amino acid sequence of the vWA domain (SEQ ID NO. 3) of ITIH5 protein, or a variant thereof, wherein said variant is at least 85% identical to the amino acid sequence of SEQ ID NO. 3, or said polypeptide comprises an amino acid sequence derived from the vWA domain (SEQ ID NO. 3) or from said variant.

In a further aspect, embodiments of this disclosure relate to isolated polypeptides having an amino acid sequence derived from SEQ ID NO. 2, wherein said amino acid sequence derived from SEQ ID NO. 2 is a peptide having an amino acid sequence selected from the group consisting of SEQ ID NO. 8 and SEQ ID NO. 9, or a variant, fragment, analog, derivative or elongation of said peptide.

In a further aspect, embodiments of this disclosure relate to isolated polypeptides having an amino acid sequence derived from SEQ ID NO. 3, wherein said amino acid sequence derived from SEQ ID NO. 3 is a peptide having an amino acid sequence selected from the group consisting of SEQ ID NO. 4, SEQ ID NO. 5, SEQ ID NO. 6 and SEQ ID NO. 7, or a variant, fragment, analog, derivative or elongation of said peptide.

In still another aspect, embodiments of this disclosure provide nucleic acids encoding said isolated polypeptides and/or peptides, as well as vectors and host cells comprising such nucleic acids.

In other aspects, this disclosure relates to compositions comprising an isolated polypeptide and/or peptide as described herein, wherein said compositions may be useful for, or used in therapeutic applications. In one advantageous embodiment, the composition is used as a therapeutically composition for the treatment of cancer, in particular of breast cancer.

In still another aspect, embodiments of this disclosure provide medicaments and compositions suitable for the treatment of cancer comprising at least a polypeptide and/or a peptide according to the present disclosure in combinations with a pharmacologically acceptable carrier or diluent for the use in treating breast cancer, lung cancer, colon cancer, bladder cancer, hepatocellular carcinoma, prostate cancer, kidney cancer, uterine cervical cancer or leukemia.

In particular, embodiments of the present disclosure pertains to medicaments suitable for the treatment of cancer, in particular for the use in treating breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas, wherein the medicament comprises an isolated polypeptide according to any one of claims 1 to 3 in combinations with a pharmacologically acceptable carrier or diluent.

Furthermore, embodiments of the present disclosure pertains to the use of the disclosed polypeptides and/or peptides for the use in the treatment of cancer, in particular for the use in treating breast cancer, lung cancer, colon cancer, bladder cancer, hepatocellular carcinoma, prostate cancer, kidney cancer, uterine cervical cancer or leukemia.

In particular, embodiments of the present disclosure pertains to isolated polypeptide for the use in the treatment of cancer, wherein said polypeptide is a fragment of the naturally occurring ITIH5-protein comprising an amino acid sequence of SEQ ID NO. 2, or a variant thereof, wherein said variant is at least 85% identical to the amino acid sequence of SEQ ID NO. 2, and wherein said fragment is less than 700 amino acids in length.

Furthermore, embodiments of the present disclosure pertains to isolated peptides according to the present disclosure for the use in treating cancer, in particular for the use in treating breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas.

Furthermore, embodiments of the present disclosure pertains to methods of the for the use in the treatment and/or preventing of cancer, in particular for the use in treating and/or preventing breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas, comprising administering an effective amount of an isolated polypeptide according to the present disclosure or an isolated peptide according to the present disclosure or a nucleic acid molecule according to the present disclosure to a cell or animal in need thereof.

Before the disclosure is described in detail, it is to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 2 is a diagram showing the performance of the recombinant 1-681_ITIH5 in vitro. A) Persisting stability of 1-681_ITIH5 over 48 h in vitro. 1 µg/ml of 1-681_ITIH5 was added to the supernatant of MDA-MB231 breast cancer cells. To the given time points 1 ml of the supernatant was harvested and non-degraded 1-681_ITIH5 was isolated and analyzed by western blotting (as shown). B) LDH cytotoxicity assay. Recombinant 1-681_ITIH5 shows no unspecific cytotoxicity in MDA-MB231 breast cancer cells after 72 h when compared to controls.

FIG. 7 shows the amino acid sequence of the isolated polypeptide 1-681_ITIH5 (SEQ ID NO: 1).

FIG. 8 shows the amino acid sequence of the "VIT" domain of the inter-alpha-trypsin inhibitor heavy chain (ITIH) proteins (SEQ ID NO: 2).

FIG. 9 shows the amino acid sequence of the "vWA" domain of the inter-alpha-trypsin inhibitor heavy chain (ITIH) proteins (SEQ ID NO: 3).

FIG. 10 shows the amino acid sequences of isolated peptides A) #26 (SEQ ID NO: 8) and B) #32 (SEQ ID NO: 9) derived from the ITIH5 VIT-domain (SEQ ID NO: 2)

FIG. 11 shows the amino acid sequences of isolated peptides A) #98 (SEQ ID NO: 4), B) #102 (SEQ ID NO: 5), C) #108 (SEQ ID NO: 6) and D) #111 (SEQ ID NO: 7) derived from the ITIH5 vWA domain (SEQ ID NO: 3)

Figure 1:
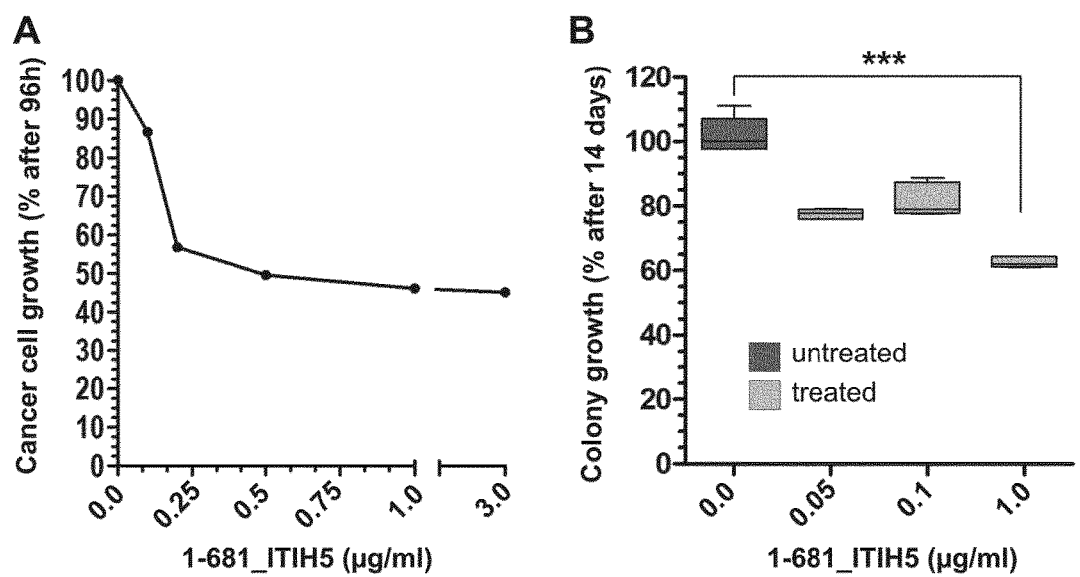
FIG. 1 present diagrams showing the tumor suppressive impact of a recombinant ITIH5 protein fragment comprising amino acids 1 to 681 (in the following named: 1-681_ITIH5) on aggressive MDA-MB231 breast cancer cells. A) Dose dependent inhibition of tumor cell growth ("dose response curve") mediated by recombinant 1-681_ITIH5 treatment in vitro using a short-term cell number assay. B) Densitometrical evaluation of colony growth after 14 days in culture. Application of 1-681_ITIH5 significantly impairs colony growth in vitro. ***p<0.001 (Dunn's multiple comparison test).

comprising only the vWA domain (i.e. comprising 213 amino acids; named in the following: "213_vWA") on breast cancer cells. Dose dependent inhibition ("dose response curve") of MDA-MB231 breast cancer cells mediated by recombinant 213_vWA (black line) was compared to scrambled control proteins (grey line) in vitro using a short-term cell number assay.

DETAILED DESCRIPTION OF THE INVENTION

The present application discloses therapeutically useful isolated polypeptides and peptides, in particular of smaller peptides suitable as human and/or animal drugs against cancer. The polypeptides and smaller peptides disclosed herein are therapeutic agents for use in prophylaxis or treatment of cancer diseases, in particular of breast cancer. The inventors have identified a number of therapeutic polypeptides and peptides derived from the vWA domain and/or the VIT-domain comprised in human ITIH-proteins. The present disclosure also encompasses compositions, in particular pharmaceutical compositions and medicaments. Accordingly, the present disclosure includes compositions of polypeptides/peptides, nucleic acids coding therefore, and/or recombinant nucleic acids into which has been inserted a nucleic acid coding for a polypeptide/peptide of the present disclosure. Said compositions and medicaments may also comprise a pharmacologically acceptable carrier or diluent.

As hereinbefore mentioned, the inventors have identified and characterized novel polypeptides and smaller peptides, wherein said polypeptides are fragments of a naturally occurring ITIH5-protein comprising the vWA domain (SEQ ID NO. 3) and/or the VIT domain (SEQ ID NO. 2) of the naturally occurring ITIH5 protein, wherein the polypeptide is a fragment and not the full-length ITIH5 protein. Furthermore, the inventors identified and characterized effective peptides, derived from said domains, and nucleic acids encoding these novel polypeptides and peptides.

In particular, the present disclosure pertains to an isolated polypeptide having a growth inhibitory effect on human cancer cells, wherein said polypeptide is a fragment of the naturally occurring ITIH5-protein, and wherein said fragment consists of SEQ ID NO. 2, or a variant thereof, wherein said variant is at least 85% identical to the amino acid sequence of SEQ ID NO. 2.

It is known that members of the group of "inter-alpha-trypsin inhibitor heavy chain" (ITIH) proteins are secreted molecules responsible for maintaining the structural integrity of extracellular matrix (ECM) structures (Zhuo L et al, 2004, J. Biol. Chem. 279: 38079-38082). Remodeling of the ECM network that consists of a variety of different structural components such as collagens or hyaluronans plays a crucial role in the progression of tumors by promoting metastasis (Lopez J I et al, 2005, Cancer Res. 65: 6755-6763). ITIH-molecules are able to covalently bind to hyaluronan and, thus, to form cable like structures that are thought to stabilize the ECM network (Salier J P et al, 1996, Biochem J 315 (Pt 1): 1-9). As a consequence, it is thought that ITIH molecules serve as potential barrier for malignant progression (Hamm A et al, 2008, BMC Cancer 8: 25).

Previously, the fifth heavy chain member of the ITI family, namely ITIH5, was shown to be down regulated on the expression level in human breast cancer (Himmelfarb M et al, 2004, Cancer Lett. 204: 69-77). ITIH5 down regulation is due to hypermethylation of its gene promoter and is associated with clinical parameters of malignant progression predicting reduced recurrence-free as well as overall patient survival (Veeck J et al, 2008, Oncogene 27: 865-876).

Surprisingly, the isolated polypeptides and peptides according to the present disclosure suppress the growth of human tumor cells when applied exogenously. The experiments shown in the present disclosure indicate that the polypeptides having the amino acid sequence of SEQ ID NO. 1 and in particular of polypeptides having the amino acid sequence of SEQ ID NO. 2 show strong growth suppressing activities on human tumor cells.

In particular, isolated polypeptides having an amino acid sequence derived from SEQ ID NO. 1 like isolated polypeptides having the amino acid sequence of SEQ ID NO. 2 or SEQ ID NO. 3 show such a strong effect. Furthermore, peptides derived from SEQ ID NO. 1, in particular derived from SEQ ID NO. 2 or SEQ ID NO. 3 like small peptides having an amino acid sequence of SEQ ID NO. 4, SEQ ID NO. 5, SEQ ID NO. 6 or SEQ ID NO. 7 are very effective. Thus, the isolated polypeptides and in particular the smaller peptides according to the present disclosure may be used as new anti-cancer drugs.

According to the present disclosure, the therapeutic agents may be an isolated nucleic acid encoding SEQ ID NO. 1, SEQ ID NO. 2 and/or SEQ ID NO. 3, or variants thereof, a protein including polypeptides or oligopeptides comprising said sequences, or variants thereof, or in an advantageous embodiment a small peptide derived from SEQ ID NO. 1, SEQ ID NO. 2 and/or SEQ ID NO. 3, or from variants thereof.

In an advantageous embodiment, the therapeutic agent is an isolated polypeptide or a small peptide according to the present disclosure for the use in prophylaxis, treatment and/or diagnosis of a disease or disorder based inter alia on an altered ITIH5 expression. In an advantageous embodiment the disease is a colon cancer, lung cancer, prostate cancer, stomach cancer, bladder cancer, renal cell cancer, liver cancer, pancreatic cancer and in particular breast cancer. Therefore, in advantageous embodiment the isolated polypeptide and/or the small peptides according to the present disclosure may be useful for the treatment of breast cancer.

As mentioned above, embodiments of the present disclosure pertains to isolated polypeptides having a growth inhibitory effect on human cancer cells, wherein said polypeptide is a fragment of the naturally occurring ITIH5-protein, and wherein said fragment comprises SEQ ID NO. 2 and/or SEQ ID NO. 3, or variants thereof The term "fragment of the naturally occurring ITIH5 protein" as used herein refers to a continuous part of the natural full-length ITIH5 protein with or without mutations, which is separate from and not in the context of a full-length ITIH5 protein. It may be one or more structural/topographical or functional subunit of a full-length or complete ITIH5 protein, however comprising the vWA-domain and/or the VIT-domain. The term "fragments" expressly excludes polypeptides corresponding to full-length amino acid sequences of an ITIH-protein protein like ITIH1, ITIH2, ITIH3, ITIH4, ITIH5 or ITIH6 but also include short peptides derived from SEQ ID NO.1, in particular from SEQ ID NO.2 or SEQ ID NO.3, or from variants thereof, wherein said variants are at least 85% identical to the amino acid sequence of SEQ ID NO. 1, SEQ ID NO.2 or SEQ ID NO.3. Therefore, the term "fragment" refers to any subject peptide or polypeptide having an amino acid residue sequence shorter than that of a wild-type ITIH5 protein or any other protein from the ITIH-protein family. For example, in some embodiments of the present disclosure fragments having an amino acid sequence of less than 90%, in particular less than 85%, in particular less than 80%, in particular less than 70% of the parent full-length ITIH-protein, in particular ITIH5, are used. In an advantageous embodiment, the isolated polypeptide having a growth inhibitory effect on human cancer cells according to the present disclosure is a recombinant isolated polypeptide that includes the amino acids 1-681 (SEQ ID NO. 1) of the full-length ITIH5 protein, which is 942 amino acids in length. In the following this protein fragment is named "1-681_ITIH5". Therefore, in an advantageous embodiment, the isolated polypeptides according to the present disclosure are less than 700 amino acids in length.

Therefore, embodiments of the present disclosure pertain isolated polypeptides having a growth inhibitory effect on human cancer cells, wherein said polypeptide is a fragment of the naturally occurring ITIH5-protein, and wherein said fragment comprises an amino acid sequence derived from SEQ ID NO. 1.

The 1-681_ITIH5 (SEQ ID NO. 1) comprises distinct protein domains (i.e. the "VIT" and the "vWA" domain) that share different homologies among the heavy chain members.

The vault protein inter-alpha-trypsin (VIT) domain described here is found to the N-terminus of a von Willebrand factor type A domain (PF00092) in ITI heavy chains (ITIHs) and their precursors (Himmelfarb M, Klopocki E, Grube S, Staub E, Klaman I, Hinzmann B, Kristiansen G, Rosenthal A, Durst M, Dahl E; Cancer Lett 2004; 204:69-77). In an advantageous embodiment, the VIT-domain comprises the amino acid of SEQ ID NO. 2.

The von Willebrand factor is a large multimeric glycoprotein found in blood plasma. Mutant forms are involved in the aetiology of bleeding disorders. In von Willebrand factor, the type A domain (vWF) is the prototype for a protein superfamily. The vWF domain is found in various plasma proteins: complement factors B, C2, CR3 and CR4; the integrins (I-domains); collagen types VI, VII, XII and XIV; and other extracellular proteins. Although the majority of vWA-containing proteins are extracellular, the most ancient ones present in all eukaryotes are all intracellular proteins involved in functions such as transcription, DNA repair, ribosomal and membrane transport and the proteasome (Ruggeri Z M, Ware J (1993). "von Willebrand factor". FASEB J. 7 (2): 308-316. PMID 8440408). In an advantageous embodiment, the vWA-domain comprises the amino acid of SEQ ID NO. 3.

In an advantageous embodiment, the polypeptides of the present disclosure are isolated polypeptides/peptides. The term "isolated" when used in relation to a nucleic acid or protein (e.g. an protein domain), refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

As used herein the term "amino acid sequence derived from" or "peptides/polypeptides derived from" refers to polypeptides comprising the amino acid sequence of the full-length polypeptide or in particular only parts of the polypeptide, like smaller peptides. Therefore, the term refers in particular to a continuous part of the full-length amino acid sequence with or without mutations, which is separate from and not in the context of the full-length amino acid sequence. It may be one or more structural/topographical or functional subunit of a full-length or complete amino acid sequence, however derived from the vWA-domain and/or the VIT-domain of ITIH5. The term "derived from" include short peptides derived from SEQ ID NO.1, in particular from SEQ ID NO.2 or SEQ ID NO.3, or from variants thereof, wherein said variants are at least 85% identical to the amino acid sequence of SEQ ID NO. 1, SEQ ID NO.2 or SEQ ID NO.3, In particular, amino acid sequence derived from SEQ ID NO. 1, SEQ ID NO. 2 and/or SEQ ID NO. 3 are SEQ ID NO. 4, SEQ ID NO. 5, SEQ ID NO. 6 SEQ ID NO. 7, SEQ ID NO. 8 and SEQ ID NO. 9, or fragments, analogs, derivatives or elongations thereof having at least 85%, at least 90%, at least 95 or at least 99% identity to SEQ ID NO. 4, SEQ ID NO. 5, SEQ ID NO. 6, SEQ ID NO. 7, SEQ ID NO. 8 or SEQ ID NO. 9.

The phrases "amino acid sequence derived from SEQ ID NO. 2 or SEQ ID NO. 3" or "peptide(s)" as used herein mean in particular a peptide derived from SEQ ID NO. 2 or SEQ ID NO. 3 as described above and includes all analogs, derivatives, fragments and elongations thereof which maintain the ability to elicit a growth inhibitory effect on a human cancer cell. Preferably, said peptides are as shown in SEQ ID NOS: 4-9.

The term "variant" means that the amino acid sequence has been modified but retains the same functional characteristics, in particular the growth inhibitory effect on human cancer cells. A variant has a sequence identity of at least 70% or preferably at least 80%, 85%, 90%, 95%, 97% or 99% to the parent amino acid sequence.

The term "variant" refers further to a polypeptide or peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or Oalkyl derivatives. The imidazole nitrogen of histidine may be derivatized to form N-im-benzylhistidine. Also included as derivatives are those peptides which contain one or more naturally occurring amino acid derivatives of the twenty standard amino acids. For example: 4-hydroxyproline may be substituted for proline; 5-hydroxylysine may be substituted for lysine; 3methylhistidine may be substituted for histidine; homoserine may be substituted for serine; and ornithine may be substituted for lysine. Polypeptides and/or peptides comprising the vWA and/or VIT domain of ITIH5 or peptides derived from these domains also include any polypeptide or peptide having one or more additions and/or deletions or residues relative to the sequence of a polypeptide or peptide whose sequence is shown herein, so long as the requisite activity is maintained or increased.

The term "analog" includes any peptide having an amino acid residue sequence substantially identical to the sequence of the peptides shown herein in which one or more residues have been conservatively substituted with a functionally similar residue and which displays the ability to mimic a peptide according to the present disclosure. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" refers further to a polypeptide or peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or Oalkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3methylhistidine may be substituted for histidine; homoserine may be substituted for serine; and ornithine may be substituted for lysine. Polypeptides and/or peptides comprising the vWA and/or VIT domain of ITIH5 or peptides derived from these domains also include any polypeptide or peptide having one or more additions and/or deletions or residues relative to the sequence of a polypeptide or peptide whose sequence is shown herein, so long as the requisite activity is maintained or increased.

The term "elongation" refers to any subject peptide having additional amino acid residues added to either end of the peptide, preferably from 1 to 10 amino acid residues, added to either the amino-terminal and/or carboxy-terminal end of a peptide of the present disclosure.

The isolated polypeptides and smaller peptides according to the present disclosure are characterized by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still show a growth inhibitory effect on human cancer cells in any of the biological assays described herein. Substitutions are preferably "conservative". Substitutions are preferably silent substitutions in the codon usage, which will not lead to any change in the amino acid sequence, but may be introduced to enhance the expression of the protein. According to Table 1 amino acids in the same block of the second column and preferably in the same line of the fourth column may be substituted for each other. The amino acids in the second and fourth column are indicated in one-letter code.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN14, National Biomedical Research Foundation, Washington, D.C., which adapts the local homology algorithm of Smith and Waterman for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm.

Software for performing BLAST analysis is publicly available through the National Center for Biotechnology Information (NCBI), at National Institutes of Health website. Likewise, computer programs for determining percent homology are also readily available.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein.

Thus, the term "mutations" also refers to all of the changes in the polypeptide sequence encoded by the polynucleic acid sequence modified by one or more of the above-described changes.

As mentioned above, advantageous embodiments of the present disclosure relates to isolated polypeptides, wherein said polypeptides comprise the amino acid sequence SEQ ID NO. 1, or a variant thereof, wherein said variant is at least 85% identical to the amino acid sequence of SEQ ID NO. 1. In particular, said polypeptide comprises the amino acid sequence of SEQ ID NO. 2, or a variant thereof, wherein said variant is at least 85% identical to the amino acid sequence of SEQ ID NO. 2.

In further embodiments, said polypeptide comprises the amino acid sequence of SEQ ID NO. 3, or a variant thereof, wherein said variant is at least 85% identical to the amino acid sequence of SEQ ID NO: 3.

In particular, said isolated polypeptides comprise an amino acid sequence selected from the group consisting of SEQ ID NO. 4, SEQ ID NO. 5, SEQ ID NO. 6, SEQ ID NO. 7, SEQ ID NO. 8 and SEQ ID NO. 9, or a variant thereof, wherein said variant is at least 85% identical to the amino acid sequence of SEQ ID NO. 4, SEQ ID NO. 5, SEQ ID NO. 6, SEQ ID NO. 7, SEQ ID NO. 8 or SEQ ID NO. 9.

In some further embodiments, said isolated polypeptides comprise an amino acid sequence selected from the group consisting of SEQ ID NO. 4, SEQ ID NO. 5, SEQ ID NO. 6 SEQ ID NO. 7, SEQ ID NO. 8 and SEQ ID NO. 9 having at least 85%, at least 90%, at least 95 or at least 99% identity to SEQ ID NO. 4, SEQ ID NO. 5, SEQ ID NO. 6, SEQ ID NO. 7, SEQ ID NO. 8 or SEQ ID NO. 9.

As mentioned above, the present disclosure pertains also to isolated peptides having a growth inhibitory effect on human cancer cells, wherein said peptide comprises an amino acid sequence derived from SEQ ID NO. 2 or SEQ ID NO. 3.

In particular, said peptides are between 10 to 50 amino acids in length, in particular between 15 and 30 amino acids in length, in particular between 20 and 25 amino acids in length, in particular with 20 amino acids in length.

In some advantageous embodiments, an isolated peptide according to the present disclosure contains at least one folded domain.

The term "folded domain" as used herein refers to a protein sequence that is known or predicted to adapt a structurally distinct three dimensional structure of known structural class, fold or superfamily comprising at least one conformational epitope. Therefore, a folded domain is part of a structural/topographical or functional subunit of a full-length or complete protein, in particular a functional subunit derived from the VIT-domain (SEQ ID NO. 2) or from the vWA-domain (SEQ ID NO.3). It may be kept within the context of the full-length or complete protein, or may be separated therefrom, as in an isolated domain.

In some advantageous embodiments, the isolated peptides according to the present disclosure comprise an amino acid sequence selected from the group consisting of SEQ ID NO. 4, SEQ ID NO. 5, SEQ ID NO. 6 SEQ ID NO. 7, SEQ ID NO. 8 and SEQ ID NO. 9, or a fragment, analog, derivative or elongation thereof having at least 85%, at least 90%, at least 95 or at least 99% identity to SEQ ID NO. 4, SEQ ID NO. 5, SEQ ID NO. 6, SEQ ID NO. 7, SEQ ID NO. 8 or SEQ ID NO. 9, and wherein said fragment, analog, derivative or elongation is produced by recombinant or synthetic methods by substitution, insertion, addition or deletion of one or more amino acid residues.

Surprisingly, the isolated polypeptides and peptides according to the present disclosure have a growth inhibitory effect on human cancer cells, wherein the cancer cells may be breast cancer cells, lung cancer cells, colon cancer cells, bladder cancer cells, skin cancer cells, pancreatic cancer cells, stomach cancer cells, esophagus cancer cells, thyroid cancer cells, gall bladder cancer cells, hepatocellular carcinoma cells, prostate cancer cells, ovarian cancer cells, kidney cancer cells, uterine cervical cancer cells, melanoma cells, embryonic carcinoma cells, leukemia cells, glioma cells, gastrointestinal stroma cell tumors (GIST) or osteosarcoma cells. In advantageous embodiments the ITIH5 expression is lost or strongly down-regulated in said human cancer cells, for example by frequent methylation of the ITIH5 promoter.

In some embodiments, the cancer cells are the breast cancer cell lines MDA-MB231, BT20 and T47D which are model systems either for basal-type or luminal-type breast cancer. Further cell lines are A549 lung cancer cells.

The peptides of the present disclosure may be prepared as N-terminal or C-terminal fusion proteins. The fusion proteins may be prepared by fusing, through recombinant techniques or by chemical crosslinking, the N terminal or C-terminal of the peptide, and the sequence of a selected protein or selectable marker with a desired biological function. The resultant fusion proteins contain the peptide fused to the selected protein or marker protein as described herein.

The isolated polypeptides and peptides according to the present disclosure may be recombinant polypeptides or peptides. Furthermore, the encoding nucleotide sequences may be synthesized in vitro without the need for initial template DNA samples e.g. by oligonucleotide synthesis from digital genetic sequences and subsequent annealing of the resultant fragments. Desired amino acid sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops, . . . ), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

As mentioned before, a recombinant isolated polypeptide or peptide according to the present disclosure can be a recombinant product prepared using recombinant DNA methodology and expression in a suitable host cell, as is known in the art (see for example Sambrook et al., (2001) Molecular Cloning, Cold Spring Harbor Laboratory Press, Cold Spring Harbor, N.Y.). Nucleotide sequences encoding specific isolated polypeptides or peptides may be conveniently prepared, for example by polymerase chain reaction using appropriate oligonucleotide primers corresponding to the 5' and 3' regions of the domain required for isolation, and a full-length coding of the isolated protein domain sequence as template. Alternatively, the amino acid sequence of the polypeptides or peptides of the present disclosure may partially or completely be synthesized in vitro or a combination of different approaches may be used.

The present disclosure also includes isolated nucleic acid molecules encoding the polypeptides and peptides of the disclosure.

Therefore, the term "isolated" refers also to a nucleic acid substantially free of cellular material or culture medium when produced by recombinant DNA techniques, or chemical precursors, or other chemicals when chemically synthesized.

The term "nucleic acid" is intended to include DNA and RNA and can be either double stranded or single stranded. As such, these nucleic acids comprise the relevant base sequences coding for the aforementioned polypeptides and peptides.

Some advantageous embodiments of the present disclosure related to isolated nucleic acid molecules or a plurality of nucleic acid molecules encoding a) A polypeptide according to the present disclosure or a peptide according to the present disclosure,
b) for a modified form of a polypeptide according to the present disclosure or a peptide according to the present disclosure, preferably in which one or more amino acid residues are conservatively substituted,
c) a nucleic acid molecule that is capable of hybridizing to any of the nucleic acid molecules of a)-b) under stringent conditions,
d) a nucleic acid molecule that is capable of hybridizing to the complement of any of the nucleic acid molecules of a)-b) under stringent conditions,
e) a nucleic acid molecule having a sequence identity of at least 85% with any of the nucleic acid molecules of a)-d),
f) or a complement of any of the nucleic acid molecules of a)-e).

The disclosure further pertains to sequence variations from the sequences in (a) or (b), i.e., the sequences function in substantially the same manner and can be used to inhibit the cell growth of cancer cells. The variations may be attributable to local mutations or structural modifications. Nucleic acid sequences having substantial homology include nucleic acid sequences having at least 65%, more preferably at least 85%, and most preferably 90-95% identity with nucleic acid sequences that encodes an amino acid sequences selected from the group consisting of SEQ ID NO. 1, SEQ ID NO. 2, SEQ ID NO. 3, SEQ ID NO. 4, SEQ ID NO. 5, SEQ ID NO. 6 SEQ ID NO. 7, SEQ ID NO. 8 and SEQ ID NO. 9, or a variant, a fragment, analog, derivative or elongation thereof.

The term "sequence capable to hybridizing" means a nucleic acid sequence that can hybridize to a sequence of (a) or (b) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C.; 0.2×SSC at 50° C. to 65° C.; or 2.0×SSC at 44° C. to 50'C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The present disclosure is also directed to vectors comprising a nucleotide molecule of the present disclosure. The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The present disclosure is also directed to a host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell, which comprises a recombinant vector of the present disclosure may also be referred to as a "recombinant host cell".

The term "host cell(s)" refers to cell(s), which may be used in a process for purifying a recombinant protein, polypeptide or peptide in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archeobacteria, bacterial cells, insect cells, yeast, mammal cells, and/or plant cells. Bacteria envisioned as host cells can be either gram-negative or gram-positive, e.g. *Escherichia coli, Erwinia* sp., *Klebsellia* sp., *Lactobacillus* sp. or *Bacillus subtilis*. Typical yeast host cells are selected from the group consisting of *Saccharomyces cerevisiae, Hansenula polymorpha* and *Pichia pastoris*.

To express a polypeptide or peptide according to the present disclosure, a DNA encoding the polypeptide, peptide or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The polypeptide or peptide may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

Further aspects of the disclosure relate to: a method of expressing in a host cell a recombinant polypeptide or peptide as described herein from a nucleic acid molecule described herein; a host cell capable of expressing a polypeptide or peptide as described herein in appropriate culture conditions for producing said polypeptide or peptide; a method of producing a polypeptide or peptide comprising culturing such a host cell under appropriate conditions, which method may further comprise isolating said polypeptide or peptide from the cell culture, and which method may further comprise admixing the isolated polypeptide or peptide with a suitable further component (which may, for example, be another protein or an excipient or carrier).

The produced fusion proteins according to the present disclosure may be recovered, further purified, isolated, processed and/or modified by methods known in the art. For example, the polypeptide may be recovered from the nutrient medium by conventional procedures including, but not limited to, centrifugation, filtration, ultra-filtration, extraction or precipitation.

Further processing steps such as purification steps may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

Furthermore, the isolated and purified polypeptide or peptide of interest may be further processed, such as e.g. formulated into a composition, e.g. a pharmaceutical composition.

As mentioned above, a nucleic acid molecule of the present disclosure may also be chemically synthesized using standard techniques. Various methods of chemically synthesizing polydeoxynucleotides are known, including solid-phase synthesis which, like peptide synthesis, has been fully automated in commercially available DNA synthesizers (see e.g., Itakura et al. U.S. Pat. No. 4,598,049; Caruthers et al. U.S. Pat. No. 4,458,066; and Itakura U.S. Pat. Nos. 4,401,796 and 4,373,071).

The present disclosure further provides a method of the for the use in the treatment and/or preventing cancer, in particular for the use in treating and/or preventing breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas, comprising administering an effective amount of an isolated polypeptide or peptide or a nucleic acid molecule encoding a polypeptide or peptide of the present disclosure to a cell or animal in need thereof. In particular the cancer is breast cancer and/or lung cancer.

The term "animal" as used herein includes all members of the animal kingdom including mammals, in particular humans.

The term "effective amount" as used herein means an amount effective, at dosages and for periods of time necessary to achieve desired results.

More specifically, the polypeptides and peptides of the disclosure may be used in the prophylaxis or treatment of pathological conditions such as cancer, including tumor metastasis, in a mammal.

Additional embodiments of the present disclosure encompass compositions comprising the isolated polypeptides, peptides, and/or nucleic acids coding for said polypeptides or peptides, and/or recombinant nucleic acids into which has been inserted a nucleic acid sequence coding for said polypeptide(s) or peptide(s) (all of which have been herein before described). The polypeptides, peptides and nucleic acid molecules may be formulated into pharmaceutical compositions for administration to subjects in a biologically compatible form suitable for administration. By biologically compatible form suitable for administration is meant a form of the substance to be administered in which any toxic effects are outweighed by the therapeutic effects. The substances may be administered to living organisms including humans, and animals in a therapeutically effective amount. Administration of an effective amount of the pharmaceutical compositions of the present invention is defined as an amount effective, at dosages and for periods of time necessary to achieve the desired result. For example, a therapeutically active amount of a substance may vary according to factors such as the disease state, age, sex and weight of the individual, and the ability of peptide to elicit a desired response in the individual. Dosage regime may be adjusted to provide the optimum therapeutic response. For example, several divided doses may be administered daily or the dose may be proportionally reduced as indicated by the exigencies of the therapeutic situation. The active substance may be administered in a convenient manner such as by topical or transdermal application, injection (subcutaneous, intravenous, etc.), oral administration, inhalation, or rectal administration. Depending on the route of administration, the active substance may be coated in a material to protect the compound from the action of enzymes, acids and other natural conditions which may inactivate the compound.

Several modes of administration are available when using a composition containing a nucleic acid molecule encoding a polypeptide and/or peptide of the disclosure. Recombinant molecules comprising a nucleic acid sequence encoding a polypeptide and/or peptide (as described above), or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as co-precipitation and incorporation of DNA into liposomes. Recombinant molecules may also be delivered in the form of an aerosol or by lavage. The nucleic acid molecules of the disclosure may also be applied extracellularly such as by direct injection into cells. The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences (1985), Mack Publishing Company, Easton, Pa., USA). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Compositions for injection include, albeit not exclusively, polypeptides, peptides or nucleic acids in association with one or more pharmaceutically acceptable vehicles or diluents, and contained in buffered solutions with a suitable pH and iso-osmotic with the physiological fluids. Any pharmaceutically suitable diluent can be used in the composition for injections: distilled water, physiological or a salt solution, and/or a buffer solution. The composition for injections may be prepared by conventional volume-weight procedures. A certain amount of the peptide is diluted to the necessary volume with a diluent or solvent. The solution is then filtered through sterilized filters, bottled or ampouled. The resultant solution is a stable transparent liquid, and does not contain any chemical or other impurities.

Solid form preparations for oral administration can be made in the form of tablets, powders, or capsules. It may contain a medium for the active substance and other additives, including dyes, aromas, etc.

Therefore, the present disclosure pertains also to medicaments suitable for the treatment and/or preventing of cancer, in particular for the use in treating and/or preventing breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas, wherein the medicament comprises an isolated polypeptide according to the present disclosure and/or an isolated peptide according to the present disclosure in combinations with a pharmacologically acceptable carrier or diluent.

The term "pharmaceutically acceptable carrier" includes any and all solvents, dispersion media, coatings, surfactants, antioxidants, preservatives (e.g. antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

In particular the present disclosure pertains also to isolated polypeptides for the use in the treatment of cancer, wherein said polypeptide is a fragment of the naturally occurring ITIH5-protein comprising an amino acid sequence of SEQ ID NO. 2, or a variant thereof, wherein said variant is at least 85% identical to the amino acid sequence of SEQ ID NO. 2, and wherein said fragment is less than 700 amino acids in length. In particular, said fragment comprises the amino acid sequence SEQ ID NO. 1, or a variant thereof, wherein said variant is at least 85% identical to the amino acid sequence of SEQ ID NO. 1. 13. The isolated polypeptides may be used in treating cancer, in particular for the use in treating breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas. In particular, the isolated polypeptides are used in treating breast cancer and/or lung cancer.

Furthermore, the isolated peptides according to the present disclosure may be used in treating cancer, in particular for the use in treating breast cancer, lung cancer, colon cancer, bladder cancer, skin cancer, pancreatic cancer, stomach cancer, esophagus cancer, thyroid cancer, gall bladder cancer, hepatocellular carcinoma, prostate cancer, ovarian cancer, kidney cancer, uterine cervical cancer, melanoma, embryonic carcinoma, leukemia, glioma, gastrointestinal stroma cell tumors (GIST) or osteosarcomas. In particular, the isolated peptides are used in treating breast cancer and/or lung cancer.

EXAMPLES

In the following examples, materials and methods of the present disclosure are provided showing the growth inhibitory effect of the polypeptides and peptides according to the present disclosure on human cancer cells. It should be understood that these examples are for illustrative purpose only and are not to be construed as limiting this disclosure in any manner. All publications, patents, and patent applications cited herein are hereby incorporated by reference in their entirety for all purposes.

Experiment 1

An isolated polypeptide consisting of the amino acids 1 to 681 (SEQ ID NO.1) of the full-length ITIH5 protein, which is 942 amino acids in length, shows a surprisingly strong growth inhibitory effect on highly invasive breast cancer tumor cells (MDA-MB231 cell type). In the following said ITIH-fragment is named "1-681_ITIH5".

Based on the full-length ITIH5 cDNA sequence, a subsequence (cDNA position 1-2043 bp) was initially cloned into an expression vector containing a polyhistidin-tag. Afterwards the cloned plasmid construct was transfected into human HEK-293T cells in vitro. Supernatant of transfected cells was purified and recombinant 1-681_ITIH5 was isolated using His-NI-NTA chromatography. Subsequent to that 1-681_ITIH5 solution was rebuffered (buffer exchange from Imidazol to PBS) and delivered from unspecific macromolecule contaminations by ultrafiltration using Vivaspin® Centrifugal Concentrators (Sartorius Stedim Biotech, Goettingen, Germany). Highly purified 1-681_ITIH5 was used for functional in vitro validation.

Various functional readout systems were available to determine the tumor suppressive impact of 1-681_ITIH5 treatment in vitro: A) Cell number assay: Numbers of living cells were quantified after four days of culturing using the CASY cell counter and analyzer (Roche Diagnostics, Mannheim, Germany). B) XTT proliferation assay: the cell proliferation KIT (XTT) was used according to the manufacturer's recommendations (Roche). C) Colony formation assay: $1 \times 10^3$ cells were seeded into six-well plates. After 14 days of culturing grown colonies were fixed with 3.5% formaldehyde/80% methanol and stained with 0.1% crystal violet. D) Wound healing assay: a confluent monolayer was scratched with a pipette tip. Afterwards cell migration within the wounded area was analyzed by using a light microscope over three days.

Before applying 1-681_ITIH5 in vitro both the stability and the purity were tested by using a western blot analysis.

In order to ensure specificity of observed effects of 1-681_ITIH5, a LDH Cytotoxicity Detection assay (Roche) was performed according to the manufacturer's recommendations. Furthermore MDA-MB231 single cell clones were generated which stably express ITIH5 protein under a strong CMV promoter. These endogenous ITIH5-positive clones are optimal control cells, i.e. those ITIH5-positive cells should not show further sensitivity against 1-681_ITIH5 in growth inhibitory experiments.

Results

When polypeptide 1-681_ITIH5 is given to highly invasive breast cancer tumor cells (MDA-MB231 cell type) a strong dose-response dependent growth inhibitory effect can be seen in two appropriate cell culture assays, i.e. a short-term cell number assay (see FIG. 1A) and a long-term colony formation assay (see FIG. 1B). Growth inhibition up to 50% was highly significant at a protein concentration of 1 μg/ml medium but concentrations as low as 100 ng of 1-681_ITIH5/ml medium already demonstrated reproducible growth inhibition up to 20% in repeated experiments. 1-681_ITIH5 is stably preserved over at least a period of 48 hours in the supernatant of treated cancer cells (see FIG. 2A) and showed no unspecific cytotoxicity when using a LDH Cytotoxicity Detection Kit from Roche (see FIG. 2B).

Figure 3:
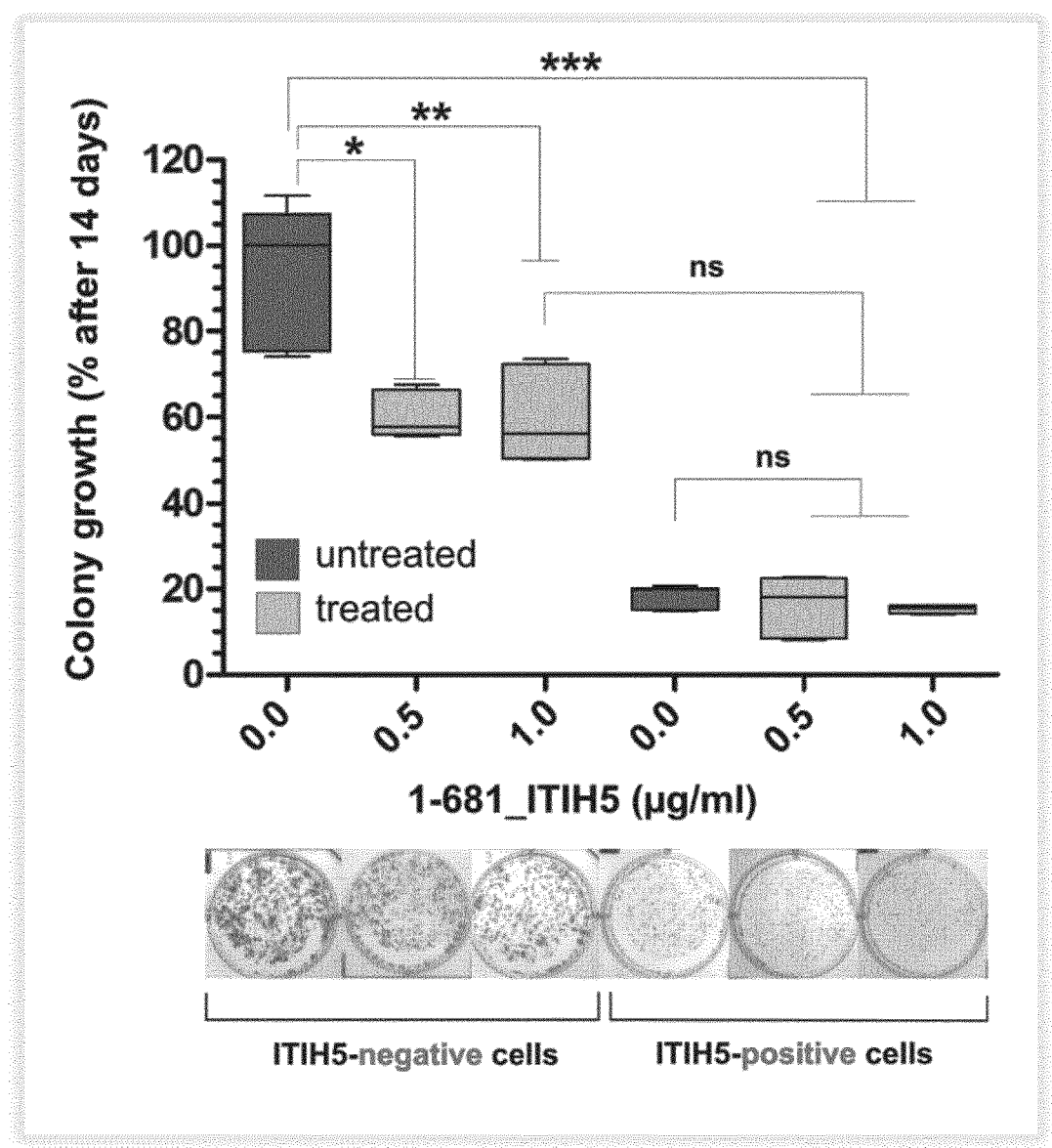
FIG. 3 presents a diagram showing that recombinant 1-681_ITIH5 mediates cell growth suppression only in ITIH5-negative MDA-MB231 breast cancer cells. Upper graph: Densitometrical evaluation of a colony formation assay shows that ITIH5-expressing single cell clones were not further inhibited by 1-681_ITIH5 treatment. Note: Differences in growth suppression between ITIH5-negative MDA-MB231 cells treated with 1-681_ITIH5 and MDA-MB231 cells stably expressing ITIH5 could be traced back to the fact that this is a comparison between a transient assay (1-681_ITIH5) and a long-term stable system (stable ITIH5 cell clones). Lower pictures: Representative wells with grown colonies are illustrated. ns: not significant, *p<0.05, p<0.01, *p<0.001 (Dunn's multiple comparison test).

In line with the latter, 1-681_ITIH5 was not able to mediate growth inhibition in MDA-MB231 endogenously ITIH5 positive cells (FIG. 3). This result suggests that recombinantly expressed 1-681_ITIH5 is acting via the same pathways as endogenously (i.e. within the tumor cell) overexpressed ITIH5 full-length protein.

Figure 4:
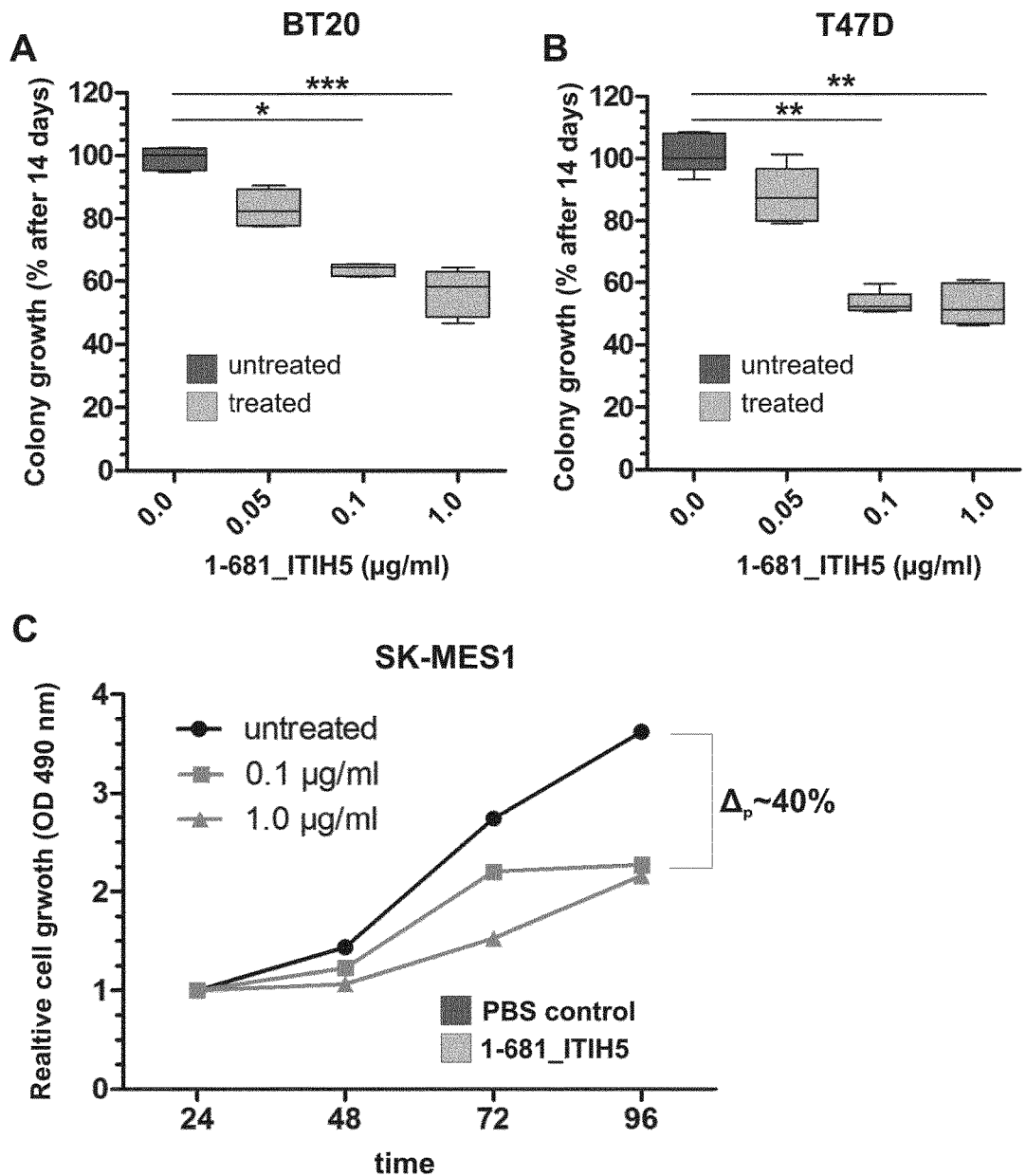
FIG. 4 present diagrams showing that 1-681_ITIH5 mediates cancer cell growth of different mammary cancer subtypes and cancer entities such as lung cancer. A) and B) Densitometrical evaluation of a colony formation assay. Application of 1-681_ITIH5 causes significantly reduced colony growth of breast cancer cell lines BT20 and T47D. C) Results from a XTT assay are shown. 1-681_ITIH5 treatment strongly mediates cell growth inhibition of SK-MES1 lung cancer cells in a dose-dependent manner in vitro. *p<0.05, p<0.01, *p<0.001 (Dunn's multiple comparison test).

Next, it was analyzed whether 1-681_ITIH5 can also suppress the growth of other breast cancer cell lines and growth of cell lines from different tumor entities like lung cancer. These experiments are shown in FIG. 4. It can be seen that 1-681_ITIH5 suppresses growth of further breast cancer cell lines like BT20 and T47D (FIGS. 4A and 4B). It also suppresses growth of the lung cancer cell lines SK-MES1 (FIG. 4C).

Figure 12:
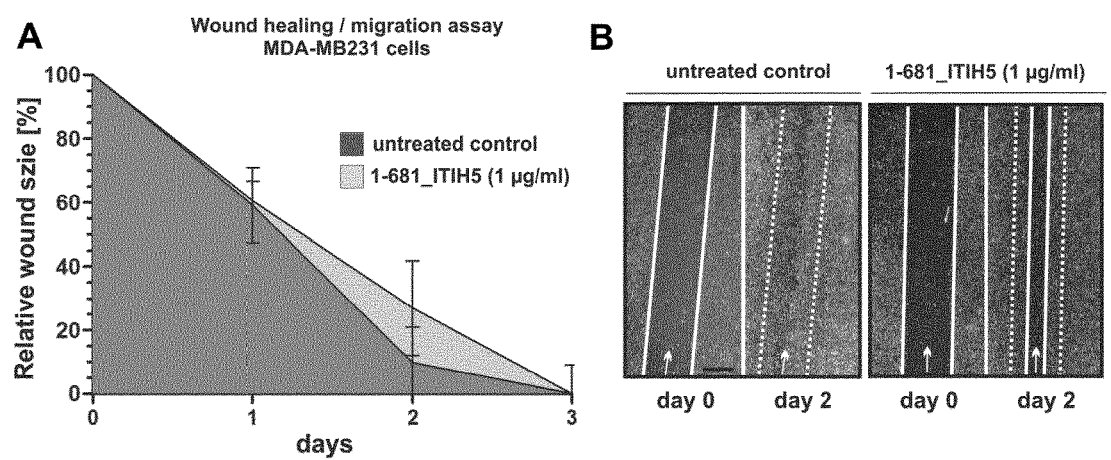
FIG. 12 presents diagrams showing that 1-681 ITIH5 inhibits tumor cell migration of aggressive MDA-MB231 breast cancer cells. A) Cell migration was analyzed by performing a scratch wound healing assay. Mean migration rate of a control cell set (untreated cells) and MDA-MB-231 treated with 1-681_ITIH5 over 3 days is shown. Vertical lines: standard deviation (S.D.) of triplicates. Cell-free area on day 0 was set as 100% and used for standardization. B) Representative images of the wound size are shown for both untreated control group and treated group. White line: wound size. Dashed line: original wound size.

Finally, 1-681_ITIH5 impairs furthermore tumor cell migration (FIG. 12), i.e. it is capable to reduce cell motility of aggressive MDA-MB231 breast cancer cells in vitro.

Therefore, 1-681_ITIH5 exhibits growth inhibitory effects on a variety of human tumor cell lines, indicating that this region 1-681 of the ITIH5 amino acid sequence harbors at least one or two domains with potent growth and migration suppressive effect on breast cancer tumor cells and potentially further human tumor cell lines.

Experiment 2

The large polypeptide 1-681_ITIH5 is for some therapeutic applications suboptimal as a drug candidate due to its size, since large polypeptides are usually more complex to handle in drug application and may undergo fast degradation in the blood system. Therefore, specific small peptide fragments derived from 1-681_ITIH5 (SEQ ID NO. 1) were generated and tested for their growth inhibitory properties on human tumor cells.

Highly purified peptides were used for functional in vitro validation. Various functional readout systems were available to determine the tumor suppressive impact of ITIH5 protein subfragments in vitro: A) Cell number assay: Numbers of living cells were quantified after four days of culturing using the CASY cell counter and analyzer (Roche Diagnostics, Mannheim, Germany). B) Colony formation assay: 1×10³ cells were seeded into six-well plates. After 14 days of culturing grown colonies were fixed with 3.5% formaldehyde/80% methanol and stained with 0.1% crystal violet. C) In order to ensure specificity of observed effects of the ITIH5 subfragments a LDH Cytotoxicity Detection Kit (Roche) was performed according to the manufacturer's recommendations. D) Wound healing assay: a confluent monolayer was scratched with a pipette tip. Afterwards cell migration within the wounded area was analyzed by using a light microscope over three days.

Results

Figure 5:
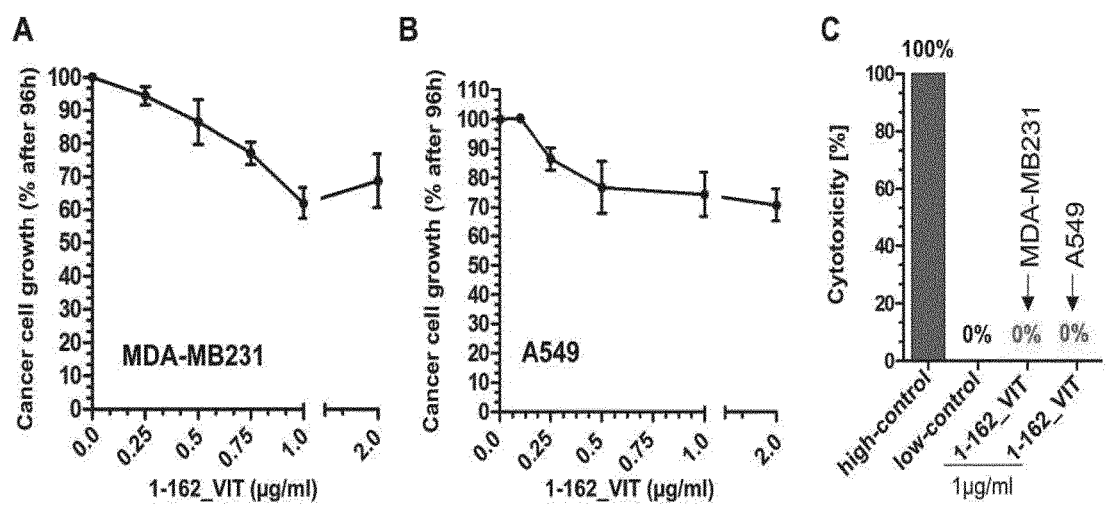
FIG. 5 presents diagrams showing the tumor suppressive impact of an isolated polypeptide (SEQ ID NO. 2) comprising only the VIT domain (i.e. amino acid 1 to 162; named in the following: "1-162_VIT") on breast cancer and lung cancer cells. A) Dose dependent inhibition ("dose response curve") of MDA-MB231 breast cancer cells mediated by recombinant 1-162_VIT treatment in vitro using a short-term cell number assay. B) Dose dependent inhibition of A549 lung cancer cells mediated by recombinant 1-162_VIT treatment in vitro using a short-term cell number assay. C) LDH cytotoxicity assay. Recombinant 1-162_VIT shows no unspecific cytotoxicity in both cell lines MDA-MB231 and A549 after 72 h when compared to controls, corroborating distinct tumor suppressive effects of 1-162_VIT.

A) FIG. 5 illustrates results for the recombinant 1-162_VIT polypeptide, named 1-162_VIT in the following. When 1-162_VIT is given to both highly invasive breast cancer tumor cells (MDA-MB231 cell line type, see FIG. 5A) and invasive lung cancer cells (A549 cell line type, see FIG. 5B) a strong dose dependent inhibition of tumor cell growth (up to 40%) can be detected using a short-term cell number assay. 1-162_VIT showed no unspecific cytotoxicity when using a LDH Cytotoxicity Detection Kit from Roche (see FIG. 5C).

Figure 13:
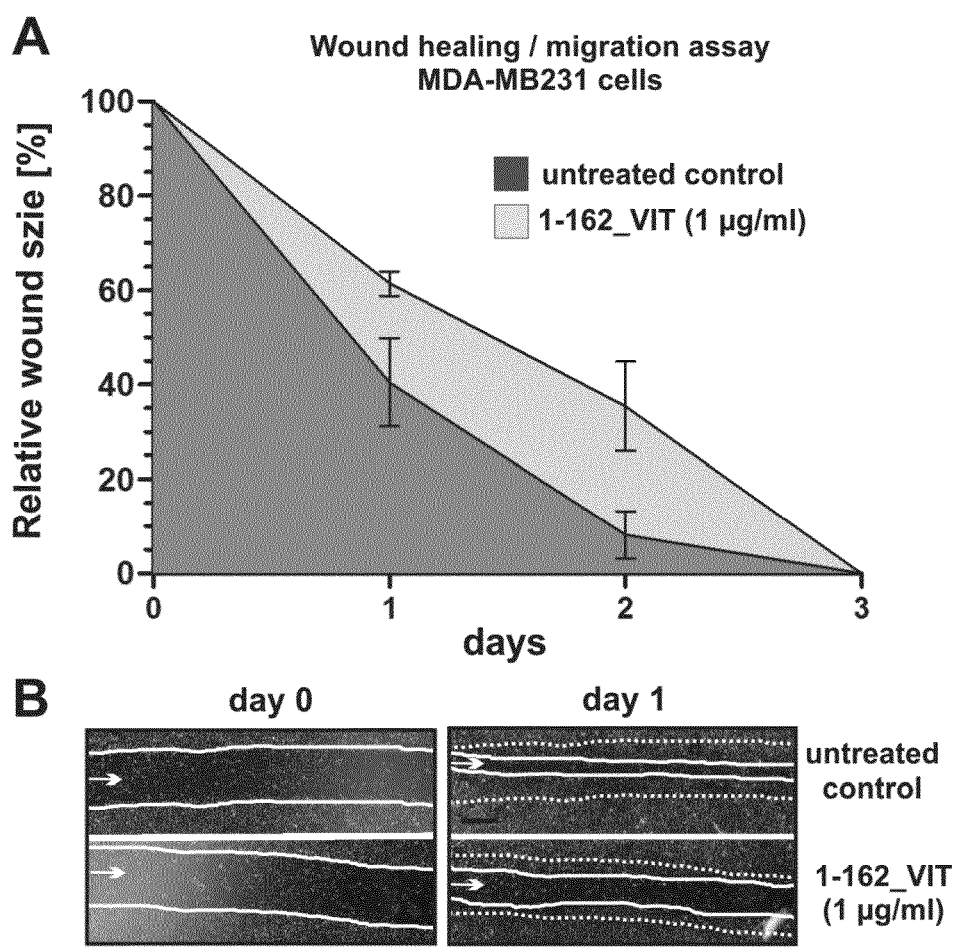
FIG. 13 presents diagrams demonstrating that 1-162_VIT inhibits tumor cell migration of aggressive MDA-MB231 breast cancer cells. A) Cell migration was analyzed by performing a scratch wound healing assay. Mean migration rate of a control cell set (untreated cells) and MDA-MB-231 treated with 1-162_VIT over 3 days is shown. Vertical lines: standard deviation (S.D.) of triplicates. Cell-free area on day 0 was set as 100% and used for standardization. B) Representative images of the wound size are shown for both untreated control group and treated group. White line: wound size. Dashed line: original wound size.

FIG. 13 shows data for the impact of recombinant 1-162_VIT on tumor cell migration of aggressive MDA-MB231 breast cancer cells in vitro. 1-162_VIT clearly suppresses cell motility of breast cancer cells already 24 hours after treatment.

Figure 6:
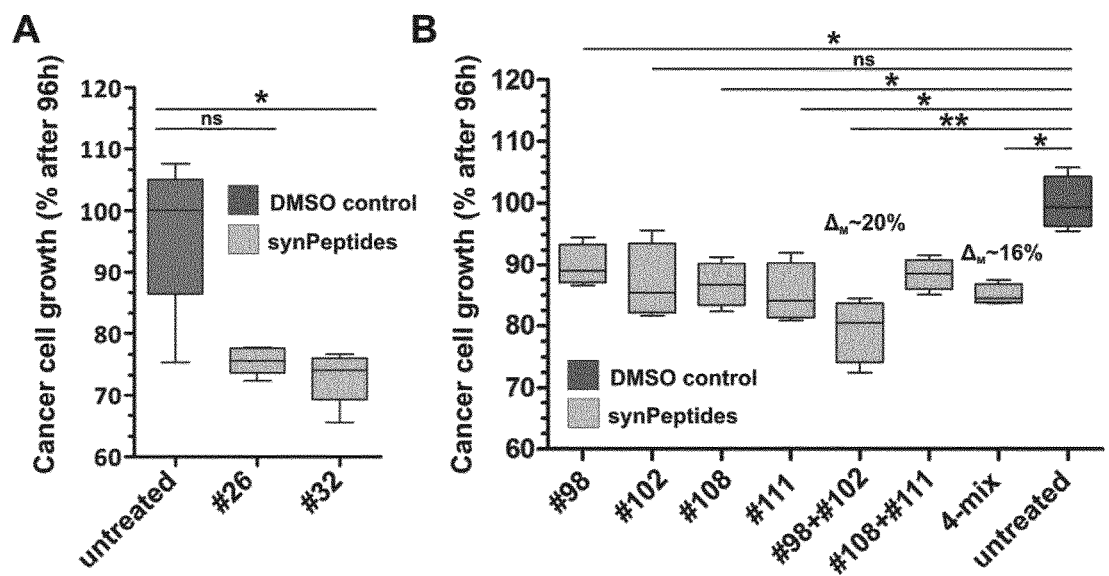
FIG. 6 presents diagrams showing the tumor suppressive impact of small peptides derived from ITIH5 on aggressive MDA-MB231 breast cancer cells. Growth inhibition mediated by chemically synthesized ITIH5-derived peptides using a short-term cell number WST assay. A) Treatment of peptides located within the VIT domain region, namely #26, #32 (300 ng/ml) B) Treatment of peptides located within the vWA domain region, namely #98, #102, #108, #111 (300 ng/ml) alone or in combination show a significant impairment of cancer cell growth in vitro. ns: not significant, *p<0.05, **p<0.01 (Mann-Whitney-Test).

B) FIG. 6 shows six small peptides (located either in the VIT (FIG. 6A) or in the vWA domain (FIG. 6B)) that were found to harbor growth inhibitory properties on human breast cancer cells when applied separately as well as in combination using a short-term XTT proliferation assay. These small protein fragments can be further optimized (stabilization, modification) to obtain suitable candidates for novel anti-tumor drugs. Use of biological drugs in targeted cancer therapy is a strongly growing area in cancer care.

Figure 14:
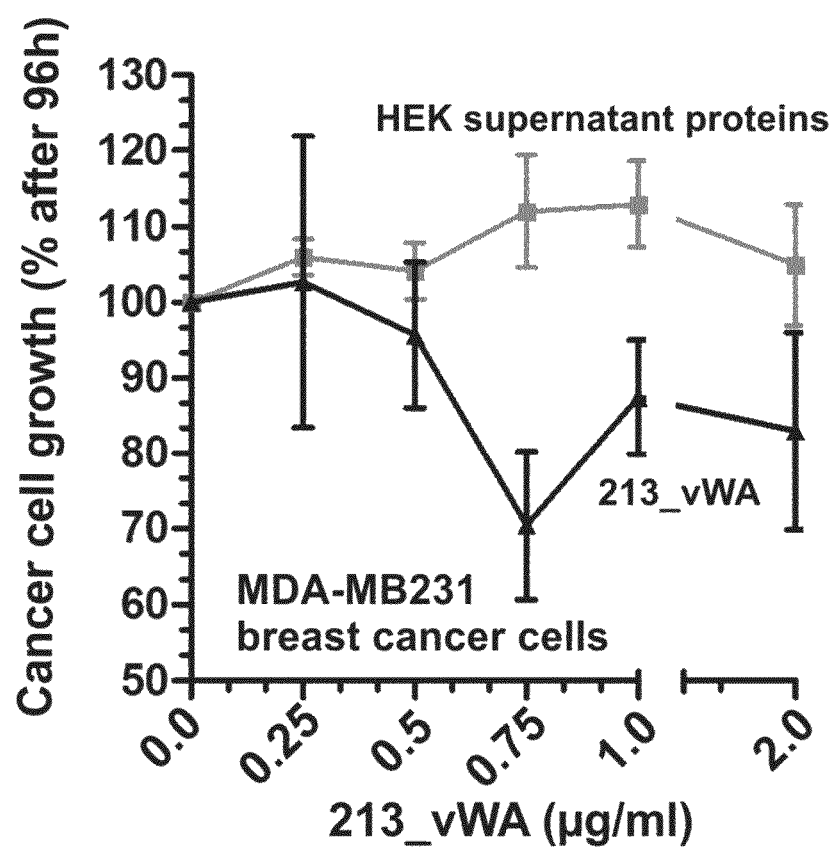
FIG. 14 presents a diagram showing the tumor suppressive impact of an isolated polypeptide (SEQ ID NO. 3)

C) FIG. 14 shows results for the recombinant 213-vWA_polypeptide, named 213_vWA in the following. When 213_vWA is applied to invasive breast cancer tumor cells (MDA-MB231 cell line) inhibition of tumor cell growth (up to 30%) was demonstrated using a short-term cell number assay.

Therefore, the recombinant 1-162_VIT (SEQ ID N0.2) polypeptide shows a significant growth inhibitory effect on a variety of human tumor cell lines and inhibits tumor cell migration. Recombinant 213_vWA (SEQ ID N0.3) and also the amino acid peptides referred to as #26, #32, #98, #102, #108, #111 exhibit a growth inhibitory impact on aggressive human breast cancer cell line MDA-MB231.

What is claimed is:

1. An isolated polypeptide having a growth inhibitory effect on human cancer cells, wherein said polypeptide consists of SEQ ID NO: 2.

2. A medicament comprising the isolated polypeptide according to claim 1 in combination with a pharmaceutically acceptable carrier or diluent.

* * * * *

SEQUENCE LISTING

```
<160> NUMBER OF SEQ ID NOS: 9

<210> SEQ ID NO 1
<211> LENGTH: 681
<212> TYPE: PRT
<213> ORGANISM: Artificial Sequence
<220> FEATURE:
<223> OTHER INFORMATION: polypeptide 1-681_ ITIH5

<400> SEQUENCE: 1

Met Leu Leu Leu Leu Gly Leu Cys Leu Gly Leu Ser Leu Cys Val Gly
1               5                  10                  15

Ser Gln Glu Glu Ala Gln Ser Trp Gly His Ser Ser Glu Gln Asp Gly
            20                  25                  30

Leu Arg Val Pro Arg Gln Val Arg Leu Leu Gln Arg Leu Lys Thr Lys
        35                  40                  45

Pro Leu Met Thr Glu Phe Ser Val Lys Ser Thr Ile Ile Ser Arg Tyr
    50                  55                  60
```

```
Ala Phe Thr Thr Val Ser Cys Arg Met Leu Asn Arg Ala Ser Glu Asp
 65                  70                  75                  80

Gln Asp Ile Glu Phe Gln Met Gln Ile Pro Ala Ala Phe Ile Thr
             85                  90                  95

Asn Phe Thr Met Leu Ile Gly Asp Lys Val Tyr Gln Gly Glu Ile Thr
                100                 105                 110

Glu Arg Glu Lys Lys Ser Gly Asp Arg Val Lys Glu Lys Arg Asn Lys
            115                 120                 125

Thr Thr Glu Glu Asn Gly Glu Lys Gly Thr Glu Ile Phe Arg Ala Ser
    130                 135                 140

Ala Val Ile Pro Ser Lys Asp Lys Ala Ala Phe Phe Leu Ser Tyr Glu
145                 150                 155                 160

Glu Leu Leu Gln Arg Arg Leu Gly Lys Tyr Glu His Ser Ile Ser Val
                165                 170                 175

Arg Pro Gln Gln Leu Ser Gly Arg Leu Ser Val Asp Val Asn Ile Leu
                180                 185                 190

Glu Ser Ala Gly Ile Ala Ser Leu Glu Val Leu Pro Leu His Asn Ser
            195                 200                 205

Arg Gln Arg Gly Ser Gly Arg Gly Glu Asp Ser Gly Pro Pro Pro
210                 215                 220

Ser Thr Val Ile Asn Gln Asn Glu Thr Phe Ala Asn Ile Ile Phe Lys
225                 230                 235                 240

Pro Thr Val Val Gln Gln Ala Arg Ile Ala Gln Asn Gly Ile Leu Gly
                245                 250                 255

Asp Phe Ile Ile Arg Tyr Asp Val Asn Arg Gln Ser Ile Gly Asp
                260                 265                 270

Ile Gln Val Leu Asn Gly Tyr Phe Val His Tyr Phe Ala Pro Lys Asp
            275                 280                 285

Leu Pro Pro Leu Pro Lys Asn Val Val Phe Val Leu Asp Ser Ser Ala
        290                 295                 300

Ser Met Val Gly Thr Lys Leu Arg Gln Thr Lys Asp Ala Leu Phe Thr
305                 310                 315                 320

Ile Leu His Asp Leu Arg Pro Gln Asp Arg Phe Ser Ile Ile Gly Phe
                325                 330                 335

Ser Asn Arg Ile Lys Val Trp Lys Asp His Leu Ile Ser Val Thr Pro
                340                 345                 350

Asp Ser Ile Arg Asp Gly Lys Val Tyr Ile His His Met Ser Pro Thr
            355                 360                 365

Gly Gly Thr Asp Ile Asn Gly Ala Leu Gln Arg Ala Ile Arg Leu Leu
        370                 375                 380

Asn Lys Tyr Val Ala His Ser Gly Ile Gly Asp Arg Ser Val Ser Leu
385                 390                 395                 400

Ile Val Phe Leu Thr Asp Gly Lys Pro Thr Val Gly Glu Thr His Thr
                405                 410                 415

Leu Lys Ile Leu Asn Asn Thr Arg Glu Ala Ala Arg Gly Gln Val Cys
                420                 425                 430

Ile Phe Thr Ile Gly Ile Gly Asn Asp Val Asp Phe Arg Leu Leu Glu
                435                 440                 445

Lys Leu Ser Leu Glu Asn Cys Gly Leu Thr Arg Arg Val His Glu Glu
            450                 455                 460

Glu Asp Ala Gly Ser Gln Leu Ile Gly Phe Tyr Asp Glu Ile Arg Thr
465                 470                 475                 480
```

```
Pro Leu Leu Ser Asp Ile Arg Ile Asp Tyr Pro Pro Ser Ser Val Val
                485                 490                 495

Gln Ala Thr Lys Thr Leu Phe Pro Asn Tyr Phe Asn Gly Ser Glu Ile
            500                 505                 510

Ile Ile Ala Gly Lys Leu Val Asp Arg Lys Leu Asp His Leu His Val
            515                 520                 525

Glu Val Thr Ala Ser Asn Ser Lys Lys Phe Ile Ile Leu Lys Thr Asp
530                 535                 540

Val Pro Val Arg Pro Gln Lys Ala Gly Lys Asp Val Thr Gly Ser Pro
545                 550                 555                 560

Arg Pro Gly Gly Asp Gly Glu Gly Asp Pro Asn His Ile Glu Arg Leu
                565                 570                 575

Trp Ser Tyr Leu Thr Thr Lys Glu Leu Leu Ser Ser Trp Leu Gln Ser
            580                 585                 590

Asp Asp Glu Pro Glu Lys Glu Arg Leu Arg Gln Arg Ala Gln Ala Leu
                595                 600                 605

Ala Val Ser Tyr Arg Phe Leu Thr Pro Phe Thr Ser Met Lys Leu Arg
            610                 615                 620

Gly Pro Val Pro Arg Met Asp Gly Leu Glu Glu Ala His Gly Met Ser
625                 630                 635                 640

Ala Ala Met Gly Pro Glu Pro Val Val Gln Ser Val Arg Gly Ala Gly
                645                 650                 655

Thr Gln Pro Gly Pro Leu Leu Lys Lys Pro Tyr Gln Pro Arg Ile Lys
                660                 665                 670

Ile Ser Lys Thr Ser Val Asp Gly Asp
            675                 680

<210> SEQ ID NO 2
<211> LENGTH: 161
<212> TYPE: PRT
<213> ORGANISM: Artificial Sequence
<220> FEATURE:
<223> OTHER INFORMATION: VIT- domain of the inter-alpha-trypsin
      inhibitor heavy chain

<400> SEQUENCE: 2

Met Leu Leu Leu Leu Gly Leu Cys Leu Gly Leu Ser Leu Cys Val Gly
1               5                   10                  15

Ser Gln Glu Glu Ala Gln Ser Trp Gly His Ser Ser Glu Gln Asp Gly
                20                  25                  30

Leu Arg Val Pro Arg Gln Val Arg Leu Leu Gln Arg Leu Lys Thr Lys
            35                  40                  45

Pro Leu Met Thr Glu Phe Ser Val Lys Ser Thr Ile Ile Ser Arg Tyr
50                  55                  60

Ala Phe Thr Thr Val Ser Cys Arg Met Leu Asn Arg Ala Ser Glu Asp
65                  70                  75                  80

Gln Asp Ile Glu Phe Gln Met Gln Ile Pro Ala Ala Ala Phe Ile Thr
                85                  90                  95

Asn Phe Thr Met Leu Ile Gly Asp Lys Val Tyr Gln Gly Glu Ile Thr
            100                 105                 110

Glu Arg Glu Lys Lys Ser Gly Asp Arg Val Lys Glu Lys Arg Asn Lys
            115                 120                 125

Thr Thr Glu Glu Asn Gly Glu Lys Gly Thr Glu Ile Phe Arg Ala Ser
130                 135                 140

Ala Val Ile Pro Ser Lys Asp Lys Ala Ala Phe Phe Leu Ser Tyr Glu
145                 150                 155                 160
```

Glu

<210> SEQ ID NO 3
<211> LENGTH: 213
<212> TYPE: PRT
<213> ORGANISM: Artificial Sequence
<220> FEATURE:
<223> OTHER INFORMATION: "vWA" domain of the inter-alpha-trypsin
      inhibitor heavy chain

<400> SEQUENCE: 3

Gly Tyr Phe Val His Tyr Phe Ala Pro Lys Asp Leu Pro Pro Leu Pro
1               5                   10                  15

Lys Asn Val Val Phe Val Leu Asp Ser Ser Ala Ser Met Val Gly Thr
            20                  25                  30

Lys Leu Arg Gln Thr Lys Asp Ala Leu Phe Thr Ile Leu His Asp Leu
        35                  40                  45

Arg Pro Gln Asp Arg Phe Ser Ile Ile Gly Phe Ser Asn Arg Ile Lys
    50                  55                  60

Val Trp Lys Asp His Leu Ile Ser Val Thr Pro Asp Ser Ile Arg Asp
65                  70                  75                  80

Gly Lys Val Tyr Ile His His Met Ser Pro Thr Gly Thr Asp Ile
                85                  90                  95

Asn Gly Ala Leu Gln Arg Ala Ile Arg Leu Leu Asn Lys Tyr Val Ala
            100                 105                 110

His Ser Gly Ile Gly Asp Arg Ser Val Ser Leu Ile Val Phe Leu Thr
        115                 120                 125

Asp Gly Lys Pro Thr Val Gly Glu Thr His Thr Leu Lys Ile Leu Asn
    130                 135                 140

Asn Thr Arg Glu Ala Ala Arg Gly Gln Val Cys Ile Phe Thr Ile Gly
145                 150                 155                 160

Ile Gly Asn Asp Val Asp Phe Arg Leu Leu Glu Lys Leu Ser Leu Glu
                165                 170                 175

Asn Cys Gly Leu Thr Arg Arg Val His Glu Glu Glu Asp Ala Gly Ser
            180                 185                 190

Gln Leu Ile Gly Phe Tyr Asp Glu Ile Arg Thr Pro Leu Leu Ser Asp
        195                 200                 205

Ile Arg Ile Asp Tyr
    210

<210> SEQ ID NO 4
<211> LENGTH: 20
<212> TYPE: PRT
<213> ORGANISM: Artificial Sequence
<220> FEATURE:
<223> OTHER INFORMATION: isolated peptide

<400> SEQUENCE: 4

Gly Asp Ile Gln Val Leu Asn Gly Tyr Phe Val His Tyr Phe Ala Pro
1               5                   10                  15

Lys Asp Leu Pro
            20

<210> SEQ ID NO 5
<211> LENGTH: 20
<212> TYPE: PRT
<213> ORGANISM: Artificial Sequence
<220> FEATURE:
<223> OTHER INFORMATION: isolated peptide

```
<400> SEQUENCE: 5

Tyr Phe Ala Pro Lys Asp Leu Pro Pro Leu Pro Lys Asn Val Val Phe
1               5                   10                  15

Val Leu Asp Ser
            20

<210> SEQ ID NO 6
<211> LENGTH: 20
<212> TYPE: PRT
<213> ORGANISM: Artificial Sequence
<220> FEATURE:
<223> OTHER INFORMATION: isolated peptide

<400> SEQUENCE: 6

Asp Ser Ser Ala Ser Met Val Gly Thr Lys Leu Arg Gln Thr Lys Asp
1               5                   10                  15

Ala Leu Phe Thr
            20

<210> SEQ ID NO 7
<211> LENGTH: 20
<212> TYPE: PRT
<213> ORGANISM: Artificial Sequence
<220> FEATURE:
<223> OTHER INFORMATION: isolated peptide

<400> SEQUENCE: 7

Lys Leu Arg Gln Thr Lys Asp Ala Leu Phe Thr Ile Leu His Asp Leu
1               5                   10                  15

Arg Pro Gln Asp
            20

<210> SEQ ID NO 8
<211> LENGTH: 20
<212> TYPE: PRT
<213> ORGANISM: Artificial Sequence
<220> FEATURE:
<223> OTHER INFORMATION: isolated peptide

<400> SEQUENCE: 8

Ser Val Lys Ser Thr Ile Ile Ser Arg Tyr Ala Phe Thr Thr Val Ser
1               5                   10                  15

Cys Arg Met Leu
            20

<210> SEQ ID NO 9
<211> LENGTH: 20
<212> TYPE: PRT
<213> ORGANISM: Artificial Sequence
<220> FEATURE:
<223> OTHER INFORMATION: isolated peptide

<400> SEQUENCE: 9

Met Leu Asn Arg Ala Ser Glu Asp Gln Asp Ile Glu Phe Gln Met Gln
1               5                   10                  15

Ile Pro Ala Ala
            20
```